United States Patent [19]

Meller et al.

[11] Patent Number: 4,696,308
[45] Date of Patent: Sep. 29, 1987

[54] CORE SAMPLING APPARATUS

[75] Inventors: Bruce T. Meller, Middleburg Heights; Michael T. Manley, Shaker Heights; Bernard N. Stulberg, Chagrin Falls, all of Ohio

[73] Assignee: The Cleveland Clinic Foundation, Cleveland, Ohio

[21] Appl. No.: 849,781

[22] Filed: Apr. 9, 1986

[51] Int. Cl.$^4$ ............................................. A61B 10/00
[52] U.S. Cl. ...................... 128/754; 128/305; 128/317; 604/158; 279/1 K; 408/204; 408/231
[58] Field of Search ............... 128/754, 305, 310, 312, 128/317; 604/158, 264, 274; 279/1 A, 1 K; 408/204, 226, 231, 232, 239 A

[56] References Cited

U.S. PATENT DOCUMENTS

| | | | |
|---|---|---|---|
| 1,150,279 | 8/1915 | Little | 408/204 |
| 2,919,692 | 1/1960 | Ackermann | 128/310 |
| 3,082,805 | 3/1963 | Royce | 146/68 |
| 3,598,108 | 8/1971 | Jamshidi | 128/310 |
| 3,613,662 | 10/1971 | Chrysostomides | 128/305 |
| 3,692,020 | 9/1972 | Schied | 128/755 |
| 3,893,445 | 7/1975 | Hofsess | 128/310 |
| 3,905,374 | 9/1975 | Winter | 128/317 |
| 4,177,797 | 12/1979 | Baylis et al. | 128/754 |
| 4,306,570 | 12/1981 | Matthews | 128/754 |
| 4,476,864 | 10/1984 | Tezel | 128/754 |
| 4,512,344 | 4/1985 | Barber | 128/305 |
| 4,543,966 | 10/1985 | Islam et al. | 128/754 |

OTHER PUBLICATIONS

"A Surgical Technique for Decompression of the Femoral Head in Osteonecrosis", by Roth, Levine & Stulberg in *Contemporary Orthodpaedics*, vol. 11, No. 3, Sep. 1985.

*Primary Examiner*—Kyle L. Howell
*Assistant Examiner*—Randy Citrin
*Attorney, Agent, or Firm*—Fay, Sharpe, Beall, Fagan, Minnich & McKee

[57] ABSTRACT

An apparatus for obtaining a core sample includes an elongate guide pin and a hollow drill element. The drill element has an open front end provided with a cutting edge and an open rear end provided with an axial engagement structure for engaging an associated driving tool. A longitudinal aperture extends from the front end of the drill element to the rear end with the aperture having a smooth uninterrupted interior periphery throughout at least a major portion of its length. A spacer slug is adapted to be positioned in the drill element longitudinal aperture. The spacer slug has a centrally disposed aperture extending longitudinally therethrough and sized so that the guide pin can extend therethrough. The spacer slug has a suitable outer diameter so that it can slide in the drill element longitudinal aperture.

22 Claims, 5 Drawing Figures

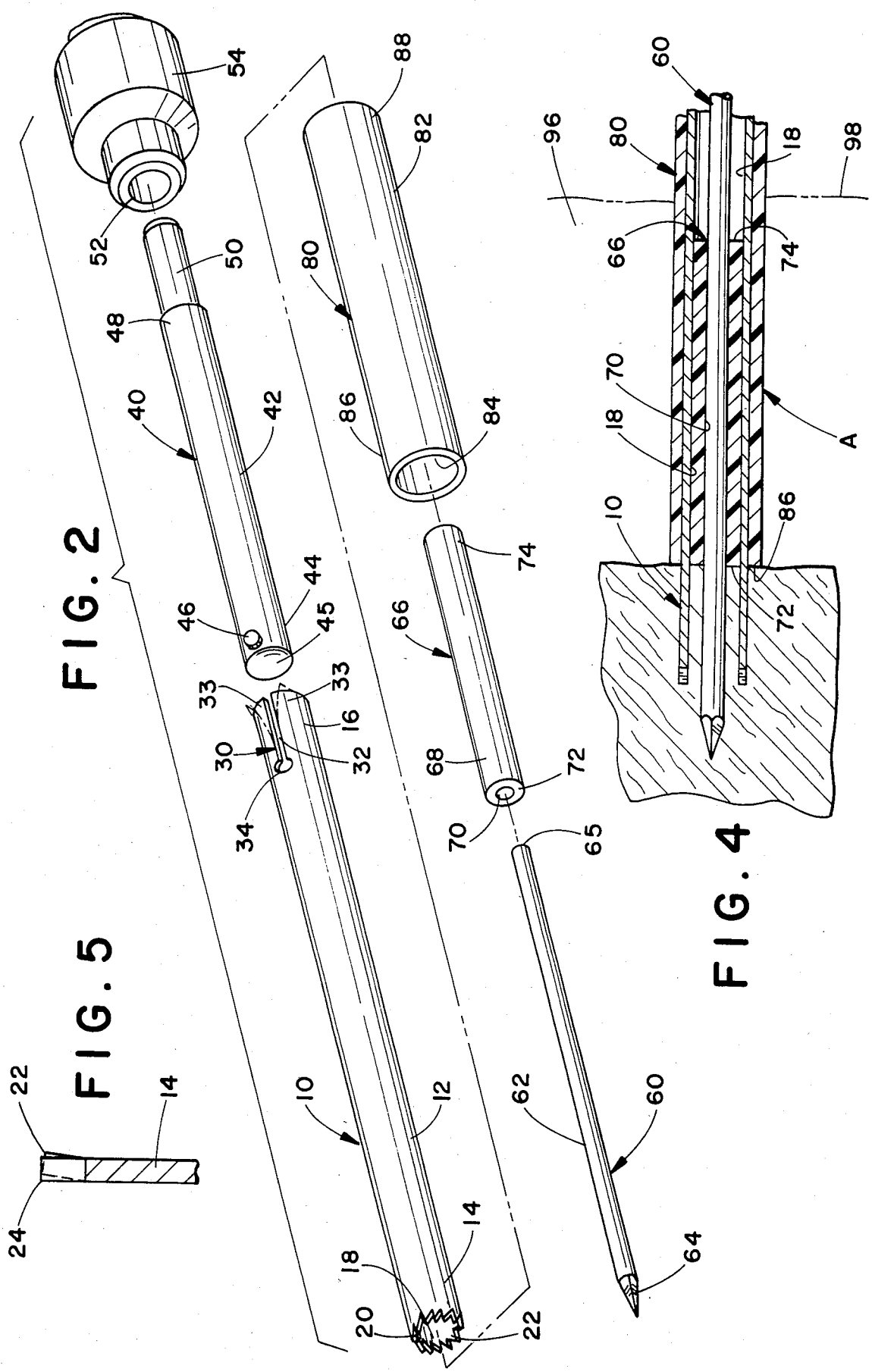

CORE SAMPLING APPARATUS

BACKGROUND OF THE INVENTION

This invention generally pertains to a core sampling apparatus. More specifically, the present invention relates to an apparatus adapted for tissue biopsies in living creatures.

The invention is particularly applicable to a device for withdrawing a core of bone from the femur of a patient in a surgical technique for decompression of the femoral head in osteonecrosis. However, it will be appreciated by those skilled in the art that the invention has broader applications and may be useful in obtaining tissue biopsies in human beings or other creatures. Moreover, the invention has still broader applications and may also be adapted for the withdrawal of core samples from various non-living objects or structures.

Osteonecrosis, i.e. bone death, especially of a "head" section of the femur, i.e. the bone situated between the pelvis and the knee in humans, can lead to severe functional disability and immobility. Usually, such osteonecrosis necessitates a replacement of the hip joint with an artificial hip. It is estimated that between 110,000 and 120,000 such hip replacement operations are performed in the United States each year.

Although numerous etiologies have been associated with the development of osteonecrosis, one common cause of the disease involves increased intraosseous pressure in the femoral head. A decompression of the femoral head can be achieved by a removal of a core section of the bone in femoral head, this is called core decompression. Removal of such a core section usually will improve blood circulation around the femoral head and will also reduce pain.

Present biopsy instruments have not, however, been found suitable for the accomplishment of such core decompression. Most biopsy needles are only adapted for cutting soft tissue such as skin, muscle, kidney, liver, etc. Even those biopsy instruments which are adapted for obtaining bone samples are not designed in such a way as to be able to quickly and safely remove a core of bone while preserving the architecture or orientation of tissue and cell types within the core for biopsy purposes while at the same time not mutilating the remaining bone in the femur or the tissue lying between the skin and the femur.

Accordingly, it has been considered desirable to develop a new and improved core sampling assembly which would overcome the foregoing difficulties and others while providing better and more advantageous overall results.

BRIEF SUMMARY OF THE INVENTION

In accordance with the present invention, a new and improved apparatus is provided for obtaining a core sample.

More particularly in accordance with the invention, the apparatus comprises an elongate guide pin and a hollow drill element. The drill element is provided with an open front end having a cutting edge and an open rear end having axial engagement means for engaging an associated driving tool. The drill element has a longitudinal aperture extending from the front end to the rear end with the aperture having a smooth uninterrupted interior periphery throughout at least a major portion of its length. A spacer slug having a centrally disposed aperture extending longitudinally therethrough is also provided. The spacer slug aperture is sized so that the guide pin can extend therethrough. An outer diameter of the spacer slug is of an appropriate size so that the spacer slug can slide in the drill element longitudinal aperture.

In accordance with another aspect of the invention, a drill apparatus is provided for cutting and withdrawing hard tissue in the form of core sample from a living being while not harming soft tissue lying between the skin and the hard tissue.

More particularly in accordance with this aspect of the invention, the drill apparatus comprises a hollow tubular drill element provided with an annular cutting edge at a front end for cutting into the hard tissue and axial engagement means at a rear end for engaging an associated driving tool. A bore extends longitudinally between the front and rear ends of the drill element for receiving a core of the hard tissue. Guard means are provided for protecting the soft tissue between the skin and the hard tissue. The guard means comprises a hollow cylindrical sleeve having an inner diameter of sufficient size so that the drill element can extend therethrough. The sleeve is of sufficient length that it can extend longitudinally from an outer periphery of the hard tissue to a location outside of the skin.

In accordance with still another aspect of the invention, a non-reusable device is provided for extracting biopsy cores or the like.

In accordance with this aspect of the invention, the device comprises a hollow tubular body having front and rear ends and a longitudinal bore, having a smooth periphery, extending between the ends. An annular cutting edge is provided on the front end of the body and is adapted for rotary penetration into tissue. An axial engagement means is provided on the body rear end. The axial engagement means includes a slit extending from the body rear end towards the body front end with the slit terminating in an enlarged aperture which is adapted to cooperate with a protrusion of an associated adapter means to enable the tubular body to rotate. The tubular body is deformed by the detachment of the associated adapter means from the body to prevent reuse of the device.

In accordance with yet another aspect of the invention, a method is provided for obtaining a core specimen of tissue.

More particularly in accordance with this aspect of the invention, the method comprises the steps of inserting a guide pin into a selected tissue and positioning a guide slug around the guide pin. A drill element, having a serrated front end, is positioned over the guide pin and guide slug. The drill element is advanced until is contacts the selected tissue. Any misalignment of the drill element with respect to the selected tissue is prevented by the guide slug adjacent the selected tissue. The drill element is then used to drill into the selected tissue and subsequently withdrawn. A core specimen of the selected tissue is withdrawn along with the drill element.

In accordance with yet still another aspect of the invention, a method is provided for the decompression of the femoral head.

More particularly in accordance with this method, a guide pin is inserted into the femur approximately in line with the femoral neck. A guide slug is pushed onto the guide pin until the guide slug is adjacent to the femur. A drill element having a serrated front end is positioned around the guide pin and the guide slug. The drill element is advanced on the guide pin until it contacts the femur. The femur is then drilled with the drill element while the guide slug is in contact with the femur to insure the correct positioning of the drill element. Subsequently, the drill element is withdrawn and with it a core of the femur is also withdrawn thereby decompressing the femoral head.

One advantage of the present invention is the provision of a new core sampling apparatus including an elongate guide pin, a hollow tubular drill element and a spacer slug which can slip over the guide pin. The spacer slug fits inside the hollow drill element to guide it and prevents misalignment of the drill element in relation to the guide pin and consequent chattering of the drill element cutting edge on the object being sampled.

Another advantage of the present invention is the provision of a core sampling device having a guard sleeve which can be fitted over a hollow tubular drill element to protect soft tissue, located between a hard tissue meant to be sampled and the skin, from the cutting edge of the drill element.

Yet another advantage of the present invention is the provision of a core sampling device having a non-reusable drill element. The drill element is so constructed that the process of detaching the drill element from an associated driving device deforms the drill element to such an extent that it can not be reused. Reuse of the drill element in bone biopsies or the like is disadvantageous because the cutting edge of the drill element becomes dulled by repeated use leading to a ragged cut and perhaps a burning of the bone.

Yet another advantage of the present invention is the provision of a drill element having an annular serrated cutting edge on its front end. The cutting edge includes a plurality of teeth of which at least some are disposed at a different angle from the remainder of the teeth. In this way, a bone core cut by the drill element ends up to be slightly smaller than the interior diameter of the element making the bone core easy to discharge after the coring process has taken place.

Still other benefits and advantages of the invention will become apparent to those skilled in the art upon reading and understanding of the following detailed specification.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof and wherein:

FIG. 2 is an exploded perspective view of an apparatus for obtaining core samples which can be used in the process of core decompression;

FIG. 4 is an enlarged side elevational view of a section of a bone which is being drilled by the apparatus according to the present invention; and, FIG. 5 is a greatly enlarged cross-sectional view through a section of a drill element of the assembly of FIG. 2.

DETAILED DESCRIPTION OF THE PREFERRED EMBODIMENT

Figure 3:
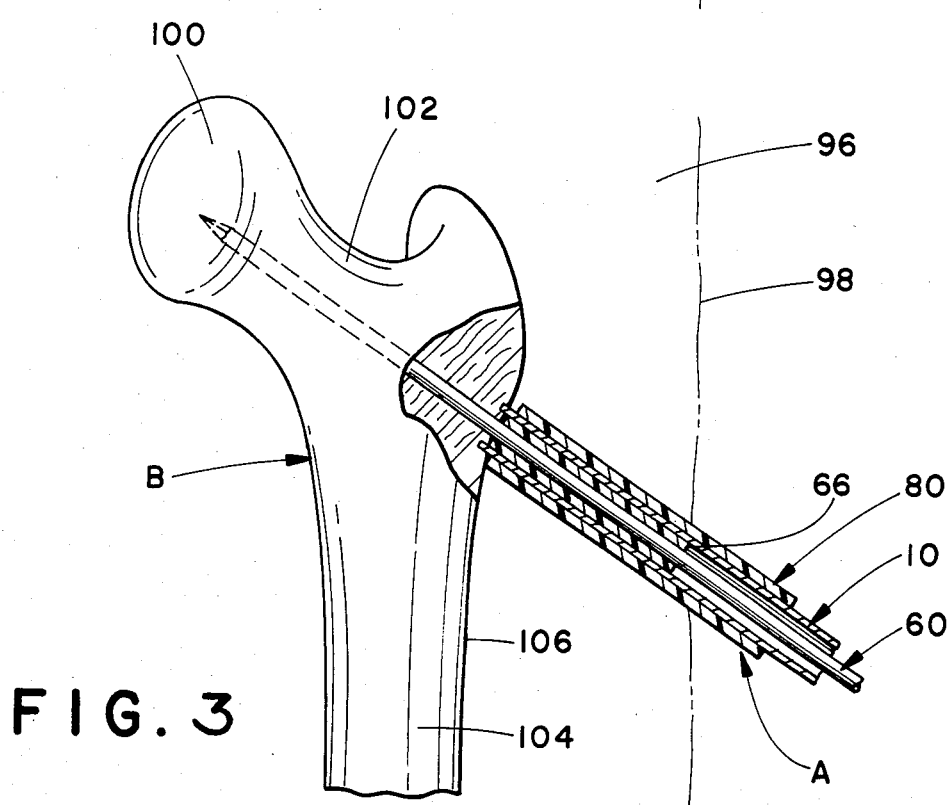
FIG. 3 is a schematic side elevational view of the femur of FIG. 1 during the process of femoral head core decompression.

Referring now to the drawings, wherein the showings are for purposes of illustrating a preferred embodiment of the invention only and not for purposes of limiting same, FIG. 3 shows the subject new apparatus A for obtaining a core sample from a femur B. While the apparatus is primarily designed for and will hereinafter be described in connection with a surgical technique for the decompression of the femoral head in osteonecrosis, it will be appreciated that the overall inventive concept could be adapted for use not only in other types of biopsies but also in other types of core sampling which do not involve a living being at all.

More particularly, and with reference now also to FIG. 2, the apparatus includes a coring drill element 10, which can also be termed a biopsy needle, having a hollow tubular drill body 12 provided with a front end 14 and a rear end 16. A longitudinal bore or aperture 18 extends from the front end to the rear end with the bore preferably having a smooth uninterrupted interior periphery throughout at least a major portion of its length. Positioned on the drill element front end 14 is an annular serrated cutting edge 20 which can be comprised of a plurality of teeth. With reference now also to FIG. 5, the teeth are preferably given several different orientations. In other words, some of the teeth are disposed at a different angle from the remainder of the teeth. In the preferred embodiment, a first tooth 22 is angled inwardly whereas a second, adjacent, tooth 24 is co-planar with the drill element body 12. Preferably, the first tooth 22 is angled inwardly approximately fourthousandths of an inch (0.0102 cm) from the second tooth 24 at the free ends of the teeth. This pattern continues around the annular cutting edge 20. The angling inwardly of every second tooth in the cutting edge 20 has been found advantageous in order to afford easy withdrawal of the core specimen from the drill body longitudinal bore 18 after the coring process is completed.

Provided on the rear end 16 of the body 12 is an axial engagement means 30 which preferably comprises a slit 32 extending from the body rear end towards the body front end. The slit 32 separates adjoining spaced sections 33 of the body rear end 16. Preferably, the slit extends longitudinally along the body and terminates in an enlarged transverse aperture 34, which can be circular, and extends from an exterior periphery of the drill element to the bore 18.

Cooperating with the drill element 10 is an adapter 40 which has a substantially cylindrical body 42 and a front end 44 provided with a forward face 45 and a transversely extending pin 46 positioned on the periphery of the adapter adjacent the forward face. A rear end 48 of the adapter 40 can be provided with a longitudinally extending projection 50 which is configured to fit within a chuck 52 of an associated driving tool 54. The pin 46 of the adapter is positionable in the aperture 34 of the drill element to connect the drill element to the associated driving tool 54 in a manner which prevents relative rotation between the adapter and the drill element and enables the drill element to be rotated by the tool.

A locating pin 60 cooperates with the drill element 10 and is positionable in the longitudinal bore 18 thereof. The locating pin has a cylindrical body 62, a pointed front end 64 which can be driven into the femur B, and a rear face 65 on its rear end. Preferably, the needle front end 64 is of the so-called trocar design having three angled faces. The pin can be a so-called Steinman pin. Of course, any other suitable type of locating pin 60 could also be utilized.

Positionable around the locating pin is a guide slug or spacer slug 66 which has a cylindrical body 68. A longitudinally extending aperture 70 runs from a front end 72 of the body 68 to its rear end 74. As shown more clearly in FIG. 4, the space slug aperture 70 is appropriately sized so that the guide pin 60 can extend therethrough. Moreover, the spacer slug 66 has an outer diameter of appropriate size so that the slug can slide in the drill element longitudinal aperture 18.

Preferably enclosing the drill element 10 is a guard means in the form of a sleeve 80. The sleeve has a cylindrical body 82 in which extends a longitudinal aperture 84 from a front end 86 of the sleeve to its rear end 88. Both the slug 66 and the sleeve 80 can be made from a suitable plastic material while the locating pin and the drill element 10 are preferably made from a metallic material.

With reference now again to FIG. 3, the sleeve 80 is meant to protect the soft tissue 96 lying between the skin 98 and the femur B from the effect the cutting edge 20 of the drill element. In this way, the drill element cutting edge 20 does not injure or wound such soft tissue, which may be muscle or the like, while the drill element is being advanced to the femur, another bone, or other hard tissue meant to be cored.

Figure 1:
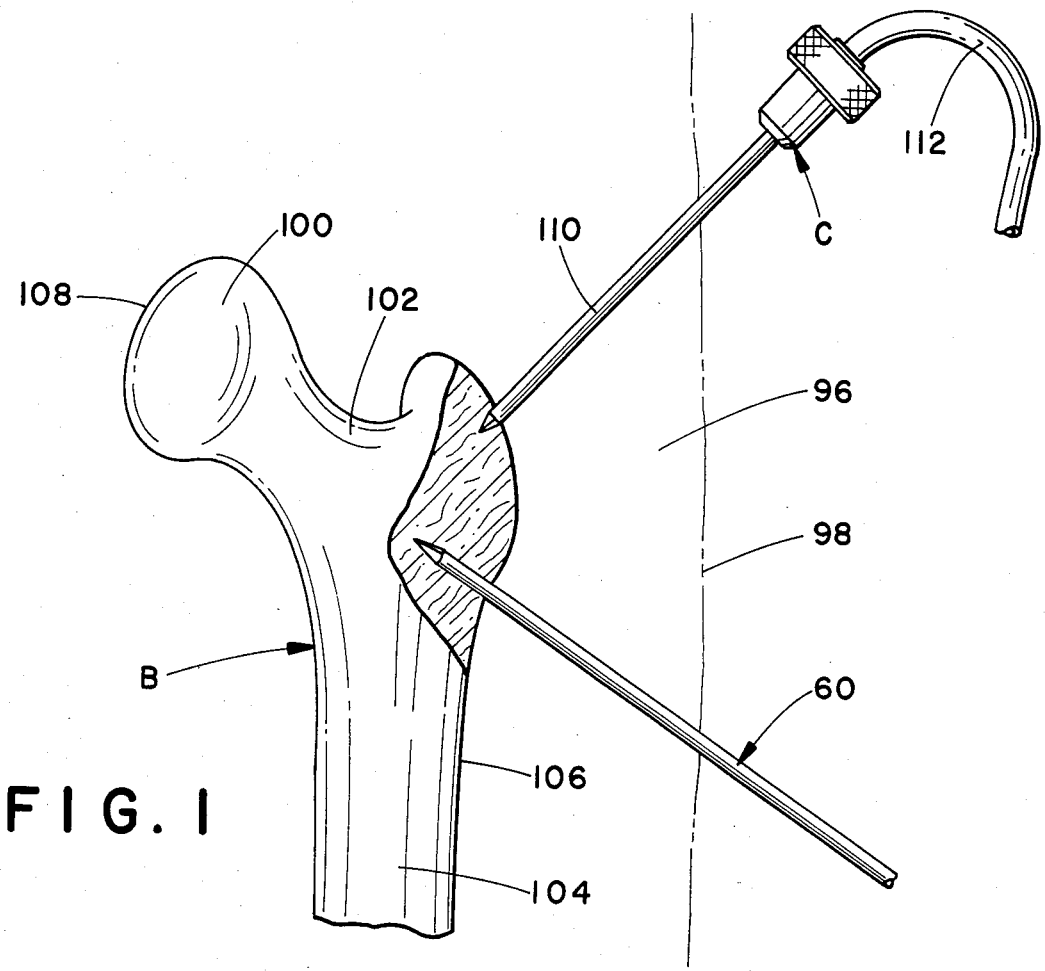
FIG. 1 is a schematic side elevational view of an upper section of a femur at the beginning stages of a process for the core decompression of the femoral head.

With reference now to FIG. 1, in order to ascertain whether the internal pressure in the femur B needs to be reduced, a pressure monitoring apparatus C is inserted in the femur. Briefly, the femur B has a femoral head 100 connected by a femoral neck 102 to a main section 104. The femur also has a proximal surface 106 on the main section and nearest the skin 98 as well as an articular surface 108 on the femoral head. The articular surface is located the furthest away from the skin and adjacent to a mating hip bone (not illustrated).

After the patient has been prepped and draped, a conventional so-called Jamshedi needle 110 of the pressure monitoring apparatus C is inserted percutaneously into the most proximal area of the femur B. This needle is inserted proximally to allow continuous monitoring of the intraoseous pressure. Intravenuous tubing 112 is connected to the needle and to an associated arterial line monitor (not illustrated) to monitor pressures. Generally, a saline load test is conducted through the needle 110, which is also termed a trocar. This involves the injection of approximately 10 cc of a saline solution. In normal hips, a slight rise in the base line pressure may be seen but this promptly returns to base line or to a level below base line. In a patient with osteonecrosis, however, the pressure will increase at least 10 mmHg from the initial pressure, will plateau, and remain elevated.

If desired, an additional confirmatory test can be done for osteonecrosis through the use of a renografin dye. Under X-ray control, 5 ml of dye is injected into the femur B through the trocar needle 110. Roentgenograms are obtained at one minute and five minute intervals. Under normal circumstances the dye should be reabsorbed into the systemic circulation within sixty seconds. However, if after five minutes stasis and/or reflux of the dye into the diaphysis is observed, the test is considered abnormal and core decompression is recommended.

For such core decompression, a second incision is then made through the skin 98 at a location spaced from the incision through which the pressure measuring needle 110 is inserted. Preferably, the muscle which forms at least a part of the tissue 96 underlying the skin 98 at the second incision is pushed out of the way and the guide pin 60 is driven partially into the femur B as shown in FIG. 1. With reference now also to FIG. 3, the guide pin 60 is driven further into the femur in a direction so as to extend into the femoral neck in line with the femoral head. This is done to allow correct orientation of the drill hole and should be performed under image intensifier control.

After the guide pin or locating pin 60 is driven into the femur B to the desired depth, the guide slug 66 can be slipped thereover and positioned adjacent the proximal surface 106 of the femur B. Subsequently, the drill element 10, can be slipped over the locating pin 60 and the guide slug 66. Simultaneously, the protective sleeve 80 is slipped over the drill element 10. It should be noted that the pressure monitoring apparatus C is not illustrated in FIG. 3, for the sake of simplicity, but it remains embedded in the femur.

As the drill element 10 is pushed through the skin 98, the protective sleeve 80 prevents contact between the drill element serrated cutting edge 20 and any soft body tissues 96. The cutting edge can, however, contact the femur proximal surface 106. At the same time, the guide slug 66 insures that the drill element 10 is correctly positioned in relation to the guide pin 60. The adapter 40 has by now been connected to the rear end 16 of the drill element by positioning the adapter pin 46 in the drill element axial engagement means aperture 34. Once a suitable driving tool 54 is connected to the adapter 40, the drill element can be rotated so that it may begin cutting into the femur B.

With reference now again to FIG. 4, as the drill element 10 cuts into a bone or other hard-tissue, in line with the guide pin 60, neither the guide slug 66 nor the protective sleeve 80 move in relation to the bone. As mentioned, suitable space is provided between the outer diameter of the guide slug 66 and the inner diameter of the protective sleeve 80 so that the drill element 10 can advance therethrough in order to cut into the bone. As mentioned, the apparatus A is useful for any type of hard tissue biopsy. It could, however, also be used for other types of core sampling.

With reference again to FIG. 3, the guide pin 60 is preferably driven into the femur B to the depth to which drill element 10 is meant to cut. When the drill element cuts to that depth, the back end 65 of the guide pin will contact the forward face 45 of the adapter 40 to prevent any further movement by the drill element into the bone. In order to accomplish this result, the guide pin and the drill element need to be correctly sized with regard to length in relation to each other. Preferably, the length of the guide pin 60 is suitably sized so that with the drill element 10 attached to the chuck adapter 40, and the guide pin positioned inside the drill element 10, when the rear face 63 of the guide pin is in contact with the forward face 45 of the adapter 40, the pointed front end 64 of the guide pin is located adjacent the cutting edge 20 of the drill element. In other words, the guide pin 60 will be somewhat shorter than the drill element 10 since the adapter extends into the drill element.

Once a core of suitable depth has been cut, and preferably such depth will bring the drill element within 5 mm of the articular surface 108 of the femur, then the drill element 10 can be withdrawn.

Withdrawal of the drill element 10 will also pull out the core sample of femoral bone as well as the guide pin 60 and the guide slug 66. The protective sleeve 80 can also then be withdrawn. With reference now again to FIG. 2, the process of disengaging the adapter 40 from the drill element 10 deforms its second end 16 by pushing the adjoining sections 33 thereof away from each other (as shown in dotted outline) thereby enlarging the slit 32 in order to allow the adapter pin 46 to be removed from the transverse aperture 34. This can be accomplished by rotating the adapter 40 out of its longitudinal alignment with the drill element 10 and forcing the two adjoining drill element sections 33 away from each other by the urging of the adapter body 42 against them at the open end of the slit 32. Thus the axial engagement means 30 also serves as a blocking means for preventing reuse of the drill element 10 by deforming it upon the disengagement of the adapter 40.

A suitable conventional means can then be used to push the core of bone out of the drill element 10 and in this way provide a biopsy specimen for analysis. It should be noted that the biopsy specimen provided by the core of bone drilled from the femur by the drill element 10 is intact at the finish of the core decompression process to provide a suitably useful core for biopsy purposes. It should, however, be mentioned that due to the presence of sclerosis in the femoral head, an excellent core biopsy specimen may not be obtained in all patients.

After withdrawal of the drill element 10 and its associated components, a repeat intraosseous pressure measurement should be recorded by the pressure monitoring apparatus C. Subsequently, the wound is closed in layers. Post-operatively, the patient is placed on a protective weight bearing regimen with auxiliary crutches for a number of weeks.

As a result of this operation, most patients experience relief of their pre-operative pain in the hip on their first post operative night because the intraosseous pressure has been decreased.

The subject invention thus provides an apparatus for obtaining a core sample. Although the invention is particularly adapted to obtain a core sample of hard tissue from a living being, it can be used to obtain core samples from any type of object. The invention has been found particularly useful in core decompression as a form of treatment for early stages of osteonecrosis of the femoral head.

The invention has been described with reference to a preferred embodiment. Obviously, modifications and alterations will occur to others upon the reading and understanding of this specification. It is intended to include all such modifications and alterations insofar as they come within the scope of the appended claims or the equivalents thereof.

What we claim is:

1. A non-reusable device for extracting biopsy cores or the like, comprising:
    a hollow tubular body having front and rear ends and a longitudinal bore extending in said body between said ends, at least a major portion of said bore having a smooth periphery;
    an annular cutting edge, adapted for rotary penetration into tissue, provided on said body front end;
    an axial engagement means provided on said body rear end, said axial engagement means including a slit extending from said body rear end towards said body front end, said slit terminating in an enlarged aperture which is adapted to cooperate with a protrusion of an associated adapter means to enable said tubular body to rotate; and,
    blocking means for preventing reuse of the device once said axial engagement means has been engaged by said associated adapter means.

2. The device of claim 1 wherein said cutting edge comprises a plurality of teeth extending around said body front end.

3. The device of claim 2 wherein some of said plurality of teeth are disposed at a different angle from the remainder of said teeth.

4. An apparatus for obtaining a core sample comprising:
    a hollow drill element having an open front end provided with a cutting edge and an open rear end provided with axial engagement means for engaging an associated driving tool, said drill element having a longitudinal aperture extending from said front end to said rear end, said aperture having a smooth uninterrupted interior periphery throughout at least a major portion of its length for accomodating a core sample;
    a spacer slug means selectively positioned within said drill element aperture for guiding said drill element, said spacer slug means having a centrally disposed aperture extending longitudinally therethrough, and having an outer diameter of appropriate size so that said spacer slug means is slidable in said drill element longitudinal aperture toward said rear end thereof as said drill element cuts the core sample; and,
    an elongate guide pin means selectively extending through said spacer slug aperture and positioned in said drill element aperture for guiding said drill element as said drill element cuts a core sample.

5. The apparatus of claim 4 wherein said guide pin means has a cylindrical external periphery of uniform diameter throughout at least the major portion of its length.

6. The apparatus of claim 4 further comprising a hollow cylindrical guard sleeve of substantially uniform internal and external diameter, said sleeve internal diameter being of suitable size so as to be able to be selectively slipped over said drill element, said guard sleeve being slidably received over said drill element and serving to protect a material through which said drill element passes, before encountering a material from which the core sample is obtained, from said drill element cutting edge.

7. The apparatus of claim 4 wherein said drill element cutting edge is annular and comprises a plurality of teeth extending around said open front end.

8. The apparatus of claim 7 wherein some of said plurality of teeth are disposed at a different angle from the remainder of said teeth.

9. The apparatus of claim 8 wherein every second tooth is angled inwardly.

10. The apparatus of claim 4 further comprising:
    a chuck adapter means for cooperating with said drill element axial engagement means to enable said drill element to be driven by a chuck of said associated driving tool; and,
    a blocking means for preventing reuse of said drill element once said axial engagement means thereof has been engaged by said chuck adapter means.

11. The apparatus of claim 10 wherein said drill element axial engagement means includes a slit extending from said drill element rear end longitudinally toward said front end, said slit terminating in an enlarged aperture which is adapted to cooperate with a protrusion of said adapter means to enable said drill element to be rotated, said drill element being deformed by the detachment of said adapter means therefrom to prevent reuse of same.

12. The apparatus of claim 4 further comprising a blocking means provided on said drill element for preventing reuse of said drill element once said axial engagement means thereof has been operatively engaged by said associated driving tool.

13. A drill apparatus for cutting and withdrawing hard tissue in the form of a core sample from a living being while not harming soft tissue lying between the skin and the hard tissue, comprising:
  a hollow tubular drill element provided with an annular cutting edge at a front end, for cutting into the hard tissue, and a rear end, a longitudinal bore extending between said front end and said rear end for receiving a core of the hard tissue;
  means for guiding said drill element cutting edge as it cuts into the hard tissue; and,
  guard means for protecting the soft tissue between the skin and the hard tissue, said guard means comprising a hollow cylindrical sleeve having an inner diameter of sufficient size that said drill element can extend therethrough.

14. The apparatus of claim 13 wherein said means for guiding comprises:
  an elongate trocar pin which is driven into the hard tissue to guide the drill element, said pin extending longitudinally in said drill element bore; and,
  a hollow cylindrical spacer slug which has a bore extending longitudinally therethrough, a diameter of said slug bore being of sufficient size that said trocar pin can extend slidably therethrough, and an outer diameter of said slug being of sufficient size that said slug is slidable in said drill element longitudinal bore as said drill element cuts the core sample said guard means being slidably received over said drill element.

15. The apparatus of claim 13 wherein said drill element cutting edge comprises a plurality of teeth extending around said front end.

16. The apparatus of claim 15 wherein every second tooth is angled inwardly by approximately 0.004 inches (0.0102 cm) to cut a core of sufficient diameter that it can be readily removed from said drill element longitudinal bore.

17. The apparatus of claim 13 wherein said means for guiding comprises a cylindrical spacer slug which is shorter than said drill element and which has an outer diameter of a sufficient size that said slug is selectively positionable in said drill element longitudinal bore and can slide toward said drill element rear end as said drill element cuts the core sample.

18. The apparatus of claim 13 further comprising a means for preventing further forward movement of said drill element cutting edge into the hard tissue past a preselected point.

19. The apparatus of claim 13 further comprising a driving means for rotating said drill element, said driving means including a chuck which is adapted to operatively engage an axial engagement means provided at said rear end of said drill element.

20. The apparatus of claim 19 further comprising a blocking means provided on said drill element for preventing reuse of said drill element once said axial engagement means thereof has been operatively engaged by said driving means.

21. The apparatus of claim 19 further comprising a chuck adapter element which interengages on a first end with said drill element axial engagement means and interengages on a second end with said driving means chuck to enable said drill element to be driven by said chuck of said driving means.

22. The apparatus of claim 21 wherein said drill element further comprises blocking means for preventing reuse of said drill element once it has been engaged by said chuck adapter.

* * * * *